(12) United States Patent
Pronovost et al.

(10) Patent No.: US 8,883,216 B2
(45) Date of Patent: Nov. 11, 2014

(54) METHODS AND CERAMIC NANOPARTICLE COMPOSITIONS FOR HEAVY METAL REMOVAL AND FOR ORAL DELIVERY OF DESIRABLE AGENTS

(71) Applicants: Allan D. Pronovost, San Diego, CA (US); Michael E. Hickey, Escondido, CA (US)

(72) Inventors: Allan D. Pronovost, San Diego, CA (US); Michael E. Hickey, Escondido, CA (US)

(73) Assignee: Red Lion Chem Tech, LLC, San Diego, CA (US)

( * ) Notice: Subject to any disclaimer, the term of this patent is extended or adjusted under 35 U.S.C. 154(b) by 70 days.

(21) Appl. No.: 13/781,537

(22) Filed: Feb. 28, 2013

(65) Prior Publication Data
US 2014/0056976 A1 Feb. 27, 2014

Related U.S. Application Data

(60) Provisional application No. 61/693,686, filed on Aug. 27, 2012.

(51) Int. Cl.
| | |
|---|---|
| *A61K 9/14* | (2006.01) |
| *B01D 15/36* | (2006.01) |
| *C02F 1/42* | (2006.01) |
| *A61K 33/24* | (2006.01) |
| *A61K 33/06* | (2006.01) |
| *A61K 45/06* | (2006.01) |
| *A61K 33/00* | (2006.01) |
| *A61K 33/40* | (2006.01) |
| *A61K 9/51* | (2006.01) |
| *C02F 1/28* | (2006.01) |
| *A61K 9/48* | (2006.01) |
| *C02F 101/20* | (2006.01) |
| *C02F 103/00* | (2006.01) |

(52) U.S. Cl.
CPC .................. *A61K 33/24* (2013.01); *A61K 33/06* (2013.01); *C02F 1/42* (2013.01); *A61K 45/06* (2013.01); *A61K 33/00* (2013.01); *A61K 33/40* (2013.01); *A61K 9/5115* (2013.01); *C02F 1/288* (2013.01); *A61K 9/4825* (2013.01); *C02F 1/281* (2013.01); *C02F 1/283* (2013.01); *C02F 1/286* (2013.01); *C02F 2101/20* (2013.01); *C02F 2103/007* (2013.01); *C02F 2305/08* (2013.01); *Y10S 977/903* (2013.01); *Y10S 977/904* (2013.01); *Y10S 977/906* (2013.01)
USPC ........... 424/489; 210/679; 210/688; 977/903; 977/904; 977/906

(58) Field of Classification Search
CPC .............................. A61K 9/1611; C02F 1/42
See application file for complete search history.

(56) References Cited

U.S. PATENT DOCUMENTS

| | | | |
|---|---|---|---|
| 5,053,139 | A | 10/1991 | Dodwell et al. |
| 6,232,367 | B1 | 5/2001 | Kobashigawa et al. |
| 2008/0084434 | A1 | 4/2008 | Sheahan et al. |
| 2008/0311182 | A1 | 12/2008 | Ferrari et al. |
| 2009/0258215 | A1 | 10/2009 | Autrey et al. |

OTHER PUBLICATIONS

Pan et al., "Highly Efficient ZRemoval of Heavy Metals by Polymer-Supported Nanosized Hydrtae Fe(III) Oxides; Behavior and XPS study", Water Res, Feb. 2010; 44(3): 815-24.*
Zhang et al, "Selective Sorption of Lead, Cadmium and Zinc Ions by a Polymeric Cation Exhanger Containing Nano-Zr(HP)3S)s", Environ Sci Technol. Jun. 1, 2008:42(11) : 4140-5.*
Choi et al., "Adsorption behaviors of ETS-10 and its variant, ETAS-10 on the removal of heavy metals, $Cu^{2+}$, $Co^{2+}$, $Mn^{2+}$ and $Zn^{2+}$ from a waste water," Microporous and Mesoporous Materials (2006) 96:157-167.
International Search Report and Written Opinion for PCT/US13/56881, mailed Jan. 10, 2014, 9 pages.

* cited by examiner

*Primary Examiner* — Carlos Azpuru
(74) *Attorney, Agent, or Firm* — Morrison & Foerster LLP

(57) ABSTRACT

Compositions and methods for heavy metal remediation are disclosed. The compositions contain ceramic nanoparticulate cation exchangers specific for at least one heavy metal as well as at least one carrier, typically a thickener, a gel forming agent and/or a cross-binding agent. The compositions may also contain chelating agents as well as beneficial agents such as vitamins and pharmaceuticals, with or without the ceramic nanoparticulate cation exchangers.

17 Claims, No Drawings

METHODS AND CERAMIC NANOPARTICLE COMPOSITIONS FOR HEAVY METAL REMOVAL AND FOR ORAL DELIVERY OF DESIRABLE AGENTS

CROSS-REFERENCE TO RELATED APPLICATION

This application claims priority from U.S. Ser. No. 61/693,686 filed 27 Aug. 2012. The content of this document is incorporated by reference herein in its entirety.

TECHNICAL FIELD

The present invention relates to materials and methods for preventing exposure of the body to heavy metals lead, mercury, arsenic, and cadmium by removing heavy metals from food and water prior to or post ingestion. More particularly the invention relates to a multi component nanoparticulate composition that sorbs heavy metals. Heavy metal chelator molecules may be included for use in removing heavy metals from soft tissues and bone. The invention also relates to the delivery of beneficial compounds using compositions of the invention.

BACKGROUND ART

Exposure to toxic heavy metals continues to be a major occupational and environmental problem around the world. Exposure occurs through environmental sources of contaminated food, water and air. The most common acute and/or chronic heavy metal toxicities are related to lead, arsenic, and mercury. These environmental heavy metals bind to hydroxyl, amino, and sulfhydryl containing groups in proteins, resulting in alterations of enzymatic activity. The affinity of metal species for sulfhydryl groups serves a protective role in heavy metal homeostasis as well. Increased synthesis of metal binding proteins in response to elevated levels of a number of metals is the body's primary defense against such poisoning.

Lead is the most significant heavy metal toxin and is related to exposure because lead has been added to paints, dyes, and gasoline. The inorganic forms of lead are absorbed through ingestion or inhalation and organic lead salts are absorbed through the skin. In adults, about 10% of an ingested dose is absorbed while children may absorb as much as 50%. Lead toxicity affects the central nervous and peripheral nervous systems and the blood, renal, gastrointestinal, cardiovascular, and reproductive systems. Lead can be found in erythrocytes (10%) and in bone (80 to 90%). Soft tissue in kidney and brain also store lead. Lead passes the placental barrier and is found in breast milk.

Chronic lead exposure is the most common toxicity in the United States. Lead poisoning from lead ingestion affects more than 2 million preschool-aged children. If left untreated heavy metal toxicities can result in significant morbidity and mortality. Encephalopathy is a leading cause of mortality in patients with both acute and chronic heavy metal toxicity.

Mercury and arsenic are also environmental poisons that can cause acute, sub-acute and chronic toxicity. Chronic toxicity is marked by neurological effects ranging from lethargy to excitement to tremor. Ligand formation is the basis for much of the transport of heavy metals throughout the body. However, some metals, like lead, compete with ionized species such as calcium and zinc to move through membrane channels in the free ionic form and follow calcium pathways to deposition in bone. Chronic exposure to mercury compounds may also lead to renal and hepatic failure and deterioration of alveolar bone with loosening of the teeth.

Exposure to arsenic is a major health concern in developing countries. The contamination of ground water is a frequent source of the arsenic and is highly prevalent in areas of gold mining. Gold miners have a high incidence of chronic arsenic poisoning.

Nearly all organ systems are involved in heavy metal toxicity. The most common include the central and peripheral nervous systems and the gastrointestinal, hematopoietic, renal, and cardiovascular systems. Lead toxicity also involves the musculoskeletal and reproductive systems. The organ systems affected and the severity of the toxicity vary with the particular heavy metal involved, the age of the individual, and the level of toxicity.

Today, toxicity due to chronic exposure to heavy metals is much more common than acute poisonings.

Even low-level environmental exposure to lead leads to a variety of chronic degenerative conditions. These conditions included cognitive disorders, hyperactivity, hypertension, renal insufficiency, cataract, cancer, and increased bone resorption. Thus, continuous exposure to low-levels of heavy metals is important to address.

Lead is a persistent metal and is still present in water, brass plumbing fixtures, soil, dust and important products manufactured with lead. Lead-based paint covers five billion square feet of nonresidential surface are in the US and almost 90 percent of the nation's bridges. Data now implicate low-level exposure and blood lead levels previously considered normal as causative factors in cognitive dysfunction, neurobehavioral disorders, neurological damage, hypertension and renal impairment. Issues surround the assessment of body lead burden and the consequences of low-level environmental exposure are critical in the treatment of chronic disease related to lead toxicity.

Another problem is the effects of these heavy metals on antioxidants. Cadmium and arsenic initiate the production of free radicals to cause tissue inflammation and genetic damage. Maintaining adequate levels of antioxidants will likely play an important role in treating heavy metal pathologies.

Nearly all fish and shellfish contain traces of mercury. The risks from mercury in fish and shellfish depend on the amount of fish and shellfish eaten and the levels of mercury in the fish and shellfish. For most people, the risk from mercury by eating fish and shellfish is not a health concern. Yet, some fish and shellfish contain higher levels of mercury that may harm an unborn baby or young child's developing nervous system. The Food and Drug Administration and the Environmental Protection Agency are advising women who may become pregnant, pregnant women, nursing mothers, and young children to avoid some types of fish and eat fish and shellfish that are lower in mercury.

Drinking water remains a major source of heavy metal exposure and is responsible for about 20 percent of the total daily exposure by the majority of the US population.

Ultrafiltration and reverse osmosis treatments produce high-quality water, but they are slow and the associated equipment and supplies are expensive. Another approach to this problem has been to use high surface area nanomaterials that actively absorb contaminants but do not restrict flow like membranes. Boehmite nanofibers that are 2 nanometers wide and 100 nanometer exhibit surface areas as high as 600 m$^2$/g. Filters fabricated from these fibers remove bacteria, viruses and endotoxins from water by irreversibly binding the pathogens or toxins. These filters also non-selectively remove a variety of metal ions and ion mixtures from water. (US2008/084434)

Some of the compositions of the invention for lead removal are designed for oral use and may deliver chelating agents through the digestive tract and also need to be excreted. Because these compositions can also be used to deliver beneficial compounds when administered orally, another aspect of the invention is delivery of such compounds using specifically designed oral compositions similar to those designed for heavy metal removal and therapy.

The two principal routes of absorption across small intestinal epithelium are paracellular and transcellular. Lipophilic drugs are absorbed by the transcellular route, whereas hydrophilic drugs are slowly absorbed via the transcellular pathway or in some cases via the paracellular route.

Bioavailability of hydrophilic compounds is poor after oral administration, due to poor absorption of hydrophilic molecules and macromolecules across the mucosal surfaces of the stomach, intestine and colon. In addition, catabolic peptidase enzymes in the gastrointestinal tract can destroy peptide and protein drugs before being absorbed. Various delivery systems have been tried to improve oral absorption of drugs including, capsules, coated tablets, liposomes, biodegradable polymers, microemulsions of surface active agents, and biodegradable hydrogels. Drug absorption has been enhanced when additives are supplied to increase solubility, such as bile salts, anionic detergents, nonionic detergents, salicylates, acyl amino acids, and acylcarnitine. Other additives, such as zonula occludens toxin (zot), have been reported to influence the nature of tight junctions between enterocytes to increase intestinal permeability of hydrophilic compounds. Classifying drugs based on their water solubility and intestinal permeability has been used to predict bioavailability of a drug after oral ingestion. In one example, to create particles capable of adhering to the walls of the small intestine, albumin and albumin combined with 1,3-diaminopropane (DAP) are used. The invention compositions solve the problems set forth above.

DISCLOSURE OF THE INVENTION

It is thus well known that heavy metals in the environment, especially in food and drinking water, are hazardous to public health. In some cases, exposure to these toxic elements may already have occurred. Various molecules that are capable of solubilizing heavy metals, such as chelators are known, but heretofore there has been no effective composition for treating elements of the environment to remove these contaminants effectively, nor are there satisfactory methods for detoxifying subjects who have already been exposed. The present invention solves these problems by providing nanoparticulate ceramic cation exchangers in suitable carriers for either external application or internal consumption.

Thus, in one aspect, the invention is directed to a composition that sorbs heavy metals which comprises a ceramic nanoparticulate cation exchanger for at least one heavy metal and at least one carrier. In some embodiments, the composition is suitable for oral consumption although in some applications such suitability is not required. Delivery methods for oral administration include tablets, capsules, powders, liquids, sublingual lozenges and chewing gum.

Preferably, in addition to the sorbent for heavy metals that is a ceramic nanoparticulate cation exchanger, other sorbents are used, including activated charcoal, derivatized chitosan, heavy metal-absorbing plant material, fumed silica, or combinations thereof.

Typically, the carrier comprises an agent for improving the handling properties of the composition and/or the behavior of the composition in the digestive tract which may be a fluid-removal agent/gel-forming agent, a miscibility agent, a thickening agent or mixtures thereof.

In some embodiments, the compositions of the invention are designed for administration to subjects who have already been exposed to heavy metal contamination and have the contamination in their blood or tissues. In these cases, a chelator that is sorbed into the system for removal of these heavy metals is included. In some embodiments, the composition may also include additional materials for which absorption is desired, such as vitamins or drugs. Thus, in some embodiments, oral delivery systems of the invention provide optimized delivery of compounds such as chelators or beneficial agents for gastrointestinal uptake. They deliver constituents to the area of the gastrointestinal tract at which it is best absorbed, and overcome physiological, biochemical, and other factors that are obstacles to optimally transfer the constituents. Suitable formulations unpackage the constituents at the desired site of use, in a manner that optimally supports absorption by the body through the lining of the gastrointestinal tract, and provide for excretion of carrier components.

In some embodiments, the invention compositions are those designed for oral delivery and excretion of carrier components wherein these compositions deliver beneficial compounds to the digestive tract. Thus, in some aspects, the invention is directed to compositions for oral delivery of beneficial compounds by absorption into the body from the digestive system wherein these compositions comprise nanoparticulate silica-based scaffolds having a surface area of at least 50 $m^2/g$, at least one beneficial compound and a miscibility agent as well as a carrier that forms a gel mass in aqueous media upon exposure to stomach and duodenal pH environment changes. Such carriers include a thickening agent and/or one or more fluid removal/gel-forming agents. These materials assure appropriate absorption and transition of the carrier components through the digestive system for excretion and/or heavy metal absorption.

MODES OF CARRYING OUT THE INVENTION

As noted above, some of the invention compositions are specifically designed for heavy metal remediation and contain ceramic nanoparticulate cation exchangers adapted for this purpose. Some of these compositions are designed for oral administration and in these compositions it is particularly desirable to provide a carrier that forms a gel in aqueous media at appropriate pH levels. This assures bulking of the composition when ingested in the presence of water and allows the carrier components to move through the digestive system to be excreted while carrying out the heavy metal remediation in the digestive tract. In some embodiments of these compositions, a chelator is also included whereby the chelating agent can be absorbed from the digestive tract into the bloodstream and remove heavy metal contaminants that are already systematically present whereby these are solubilized and removed through the kidneys. Thus, these compositions will have the property of effectively delivering the chelating agent from the digestive system to the circulation. This property is also advantageous in compositions that are simply designed to deliver beneficial compounds to the circulation after oral ingestion. Thus, some of the compositions of the invention which are designed simply for the delivery of beneficial compounds (which may include chelators) share the properties of the carrier with those compositions designed for heavy metal remediation.

Heavy Metal Remediation Agents

The invention compositions designed for heavy metal remediation employ nanocage ceramic sorbents with a high selective capacity for removal of lead, mercury and cadmium or other heavy metals from aqueous media. The substructure is composed of a nanoparticulate ceramic, cationic ion exchanger with a high specificity for heavy metal ligands, wherein these are removed even in the presence of competing ions such as calcium and magnesium. Thus, there is little interference from ions frequently found in hard water, for example. The binding of heavy metals to these ceramic supports is essentially irreversible.

Useful embodiments of this type of ceramic are illustrated by products of Engelhard (now a subsidiary of BASF). Among these products are ATS and ATC adsorbents designed to remove lead effectively from water. The ATC product includes granular activated carbon onto which the ceramic cation exchanger ATS is incorporated. These are a mixture of titanium silicate and calcium mixed salt on granular carbon (20×100, 20×50, and 20×40). Carbon is 85-98% wt. and titanium silicate/mixed salt is 2 to 15% wt. The material reduces the concentration of all metal cations present, with the highest capacity for lead. The material complies with all applicable Food, Drug and Cosmetic Acts and all relevant Food Additive Regulations. Lead can be removed from about 1,300 gallons with a 10-inch in-line filter using 140 grams ATC adsorbent. ATC Adsorbent is a free-flowing granule, grey in color from a base coconut shell material. Its surface area is 1200 m$^2$/g, its pore volume is 0.54 cm$^3$ and its pH is 6.8 at 1 percent dispersion.

Engelhard ARM 200 adsorbent is a water purification treatment agent for removal of arsenic. It is very effective in removing low levels of both As$^{+3}$ and As$^{+5}$ forms from drinking water with no pre-oxidation or pre-treatment. Arsenic removal capacity has been demonstrated to be greater than 99% even in the presence of competing ions. The ARM 200 adsorbent works well on water contaminated with arsenic levels of 1.0 mg/L or less and is available in granular or powder form. In laboratory tests, ARM 200 demonstrated six to eight times the arsenic capacity versus traditional adsorbents. Unlike some traditional water-purification technologies, it does not require high capital investment or create an arsenic disposal problem. ARM 100 adsorbent is another water purification treatment agent composed as a proprietary metal ion exchanger.

In the former compositions, heavy metal cation exchange into the ceramic nanocages is irreversible and permanent. This prohibits the future release and exposure to the host or environment.

Depending on the application, the composition will also contain a carrier which may include activated charcoal, derivatized chitosan, plant material, fumed silica, zeolite, clay or combinations. If the composition is designed for oral use, it may also contain a carrier that forms a thickened gel upon exposure to aqueous media. The nature of these components is further discussed below. In addition, such compositions may contain chelators or other beneficial compounds. The compositions may be nontoxic as would be needed if orally administered. However, if administered to materials in the environment from which they can then be removed, lack of toxicity is not needed.

The composition may be used for human, animal, aquatic species, or food crop or silage heavy metal removal.

Delivery of Beneficial (Payload) Compounds—Including Chelators

The invention also includes silica nanoparticle oral delivery system for chelates, vitamins, minerals, pharmaceuticals, nutraceuticals, food supplements and other beneficial compounds or combinations that allow for optimized delivery of these payload compounds to the body, making the payload compounds available rapidly and at the best site for adsorption. In some embodiments, the system is composed of payload compounds, a miscibility agent to link with payload compounds, other constituents to modify and optimize conditions of payload release, and a base nanoparticle binding scaffolding agent to which the miscibility agent, the payload compounds and the additional compounds incorporated into the admixture to optimize control over the conditions for releasing the payload compounds in the gastrointestinal tract.

An appropriate miscibility agent provides hydrogen bonding at two or more sites on a co-molecule to which it is adsorbed, typically through mixing, and with controlled fluidization and pH control. The system will typically include fumed silica particles, which may be agglomerated in chains, or non-agglomerated, but overall surface area of the material will be at least 50 m$^2$/g. A conventional pharmaceutical-quality inert filler material, nonaqueous liquid or solid/powder, may be added to form the final product.

As described below, miscibility agents are nonaqueous liquid long chain nonionic surfactants (or similar materials) that will minimize subsequent direct attachment of the payload constituents to the fumed silica nanoparticle binding agent, and promote initial weak hydrogen binding after primary blending of fumed silica to the mixture of miscibility agent and payload constituents. Additives may be used to precondition and stabilize the payload constituents. These include anti-stats, Zwittergent®, neutralizers, and/or stabilizers. The initial (typically aqueous) combination of payload components are blended through a preconditioning and stabilization process using the additives, resulting in a nonpolar, non-charged, condition, and are dried or lyophilized to remove the aqueous solvent. Moderate-strong hydrogen bonding cationic surfactants (as vapor, liquid, or solid) can be added to promote miscibility and control hydrogen bonding, if needed, and the addition of hydrogen-binding molecules, such as carbon tetrachloride, chloroform, and hydrocarbons) can control chain formation and particle size.

Upon solvation and primary aqueous hydration following oral ingestion, the miscibility agent releases the nanoparticle binding agent to permit exchange of weakly bound miscibility agents adsorbed with the payload constituents for highly polar water molecules at acidic pH. The fumed silica is isoelectrically neutral at pH 2.3, and at pH $<2.3$ generates a high positive net charge due to preferential hydrogen bonding of protonated water species resulting in a net positive zeta potential. At pH $<2.3$, there is active repulsion and transport of lower charged payload constituent species and miscibility agent with migration to the exterior of the gel mass for ready intestinal adsorption. Due to its thixotropic properties, the material will maintain, and continually reform, the natural gel suspension during intestinal shear forces.

The nanoparticle binding agent, typically fumed silica, described in detail below, also minimizes caking and hard settling upon hydration due to charge dispersion and dispersion in all directions to the exterior of the gel mass bordered by the lumenal wall, resulting in better distribution and absorption of the payload over a higher surface area.

A conventional pharmaceutical-quality inert filler material may be added to complete the product. Filler examples are talc in solid tablets and capsules, and alcohol in liquids (aqueous solutions are inappropriate in this application). The fumed silica binding agent may provide sufficient filler properties. If the final product is to be a nonaqueous liquid, it can be produced in gel-cap form, or as a suspension or emulsion.

Some vitamins and other therapeutic and/or preventive materials, such as Vitamins B6, B12, and folic acid (folate) do not transfer well via absorption through the intestinal wall.

Sublingual, chewing gum, or skin patch application using fumed silica particles can increase absorption without nanoparticle crossover into the vascular system.

As noted above, when ingested, the compositions are rapidly hydrated, to form a thixotropic, flexible, gel mass. As that mass travels through the gastrointestinal tract, there is a polar exchange leading to release of payload constituents. That release action is to a great extent pH-dependent, which permits control over the release point. Fluidization of the miscibility agent at pH <4.0 and body temperatures results in vitamin release in bioactive form. Active charge repulsion from the gel mass due to aqueous protonation under acidic conditions results in charge gradient migration of the payload constituents to the lumenal border. Due to that charge gradient, there is active adsorption of the payload constituents from the gel mass surface, which continually reforms to provide continued and sustained release. Eventually, as the mass proceeds to the end of the gastrointestinal tract it is voided in the feces.

Chelators

In some of the compositions of the invention, a chelator is also used. These compositions may be suitable for external application and the chelator serves as an aid for more effective removal of heavy metal ions. Chelators can also be included in compositions to be ingested and are a requisite for removal of heavy metals that have already migrated to the tissues or bloodstream, lymphatic system, CSF, or other biological fluids. Considerations with regard to these chelators and how to prepare suitable compositions containing them is dependent on their application. As noted below, many chelators available in the art have some undesirable side effects when ingested, and the invention compositions are designed to minimize these.

The discussion below is illustrative but not comprehensive of the chelators that may be used. In addition to those specifically mentioned commonly used chelating agents include DOTA.

The water-soluble chelator meso 2,3-dimercaptosuccinic acid (DMSA) appears to be a potentially safe and effective method for treating lead or arsenic poisoning, except for its lipophobic nature, a major disadvantage in its ability to remove lead from intracellular sites. A new trend in chelation therapy is to use combined treatment that includes structurally different chelators or a combination of an adjuvant and a chelator to provide better clinical/biochemical recovery in addition to lead mobilization. In the context of the present invention, safe delivery of this chelator may be achieved.

A large number of esters of DMSA have been tested. These analogues of DMSA are capable of crossing membranes and reduce the metal burden in acute and sub-chronic metal intoxication. These monoesters are more effective in the treatment of experimental induced metal intoxication.

Among the new chelators, monoisoamyl ester of DMSA (MiADMSA) was more effective than DMSA in reducing mercury and cadmium burden. Of the 3 amino-based and 4 thio-based chelators, DMSA and MiADMSA produced less oxidative stress and toxicity and induced less metal redistribution, hepatotoxicity and oxidative stress. MiADMSA may be a future drug of choice owing to its lipophilic character and the absence of any metal redistribution. Moderate toxicity after repeated administration may be reversible after the withdrawal of the chelating agent.

Combination therapy may improve results. Vitamins, essential metals or amino acid supplementation during chelation therapy provides recovery from altered biochemical states. Antioxidants may enhance the efficacy of the treatment protocol designed to mitigate arsenic induced toxicity. Co-administration of naturally occurring vitamins such as vitamin E or vitamin C during administration of a thiol chelator such as DMSA or MiADMSA may be more beneficial in the restoration of altered biochemical variables.

It has been reported that the beneficial effects of MiADMSA in mobilizing arsenic and in reducing tissue oxidative stress were achieved by combining administration of oxalic acid and MiADMSA. Other clinical studies have shown that combined administration of two chelators was more effective than either one administered alone. Mono isoamyl DMSA has also been used in combination with N acetyl cysteine as well as various fruit extracts.

The most commonly used chelating agents belong to the polyaminocarboxylic group, i.e., EDTA (ethylenediamine tetraacetic acid), which has been the mainstay of chelation therapy for many years. Other members include DTPA (diethylene triamine pentaacetic acid). Intravenous administration of this drug results in good absorption but is very painful at the injection site. Calcium and sodium salts of EDTA have toxic effects on the renal system. EDTA also chelates various essential metals in the body, particularly zinc leading to other metabolic problems. Oral administration of EDTA during pregnancy can result in teratogenic effects in animals. Absorption into the circulation, potential interaction with essential trace elements, and the stress associated with the administration of the compound were factors for inducing maternal and developmental toxicity. The compositions of the invention are designed to minimize the drawbacks of this chelator.

DPA (D-penicillamine) is a sulfhydryl containing amino acid chelator (3,3 dimethylcysteine) and is an antidote to low and mild lead poisoning. DPA can be absorbed through the gastrointestinal tract and can be administered orally.

Sodium 2,3-dimercaptopropane sulfonate (DMPS) is a chelator that occupies extracellular space and may enter cells by a specific transport mechanism. DMPS is rapidly eliminated from the body through the kidneys. No major adverse effects after DMPS administration to humans or animals have been reported, but a dose dependent increase in copper content was found in serum, liver, kidneys and spleen. Oral administration of DMPS also did not adversely affect late gestation, parturition or lactation in mature animals and fetal and neonatal development do not appear to be adversely affected. DMPS is effective for treating lead and arsenic poisoning, but less effect for removing mercury. No side effects were reported in patients treated with DMPS.

A positive correlation has been established between dietary supplementation with a number of vegetables and plant parts and the reduction of toxic effects of heavy metals.

The compositions of the invention intended for oral use are designed to provide more effective removal of heavy metal ions from potentially lipophilic regions of tissue by using more effective heavy metal chelators in a more effective manner to provide irreversible sequestration of metal ions, and to deliver the chelators in the most effective manner. Because the invention composition controls delivery, the undesired side effects of the above-listed chelators can be avoided.

Beneficial Compounds

In some embodiments, in addition to or instead of the capacity to remediate heavy metals, the compositions of the invention that are designed for oral administration may also contain desirable agents that can simultaneously be delivered to the subject. These agents include vitamins and various drugs.

A non-exhaustive list of compounds that could be delivered includes vitamins, minerals such as ascorbic acid, potassium chloride, alpha tocopherol acetate, calcium carbonate, zinc oxide, ferrous fumarate, niacinamide, pantothenate, manganese sulfate, magnesium stearate, cupric oxide, vitamin A, acetate pyridoxine hydrochloride, riboflavin, beta carotene, thiamine mononitrate sodium and potassium borates, chromium chloride, folic acid, potassium iodide, sodium selenate, sodium molybdate, sodium metavanadate, biotin, phytonadione, nickel sulfate, stannous chloride, ergocalciferol, and cyanocobalamin. Other agents include antioxidants, micronutrients, zinc, cooper, selenium, magnesium, taurine, alpha-lipoic acid, and others. In addition, protectant biomolecules from oxidative damage and micronutrients to reduce metal absorption by competing for the same binding sites may also be included.

To the extent that beneficial agents to be absorbed are included, additional components may be helpful, such as those that provide controlled delivery of the agents. These may also be duplicative with thickening agents. These materials retain fluid with functional additives in an inner core and may be dispersed in the fluid media as porous, amorphous microsphere particles (20-25 microns) with low moisture content where they absorb the functional agents and absorb water upon hydration.

Miscibility Agents

In those embodiments designed for oral delivery of beneficial compounds, including chelators, it is desirable to add a material to effect miscibility of active agents in the compositions. Generally, these are water-soluble materials with fluidization at pH <5 to facilitate release. Materials suitable generally also provide hydrogen bonding in a short chain molecule such as glycerol, or polymers polyethylene glycol, polysorbate esters and the like.

As noted above, orally administrable compositions of the invention that are designed to deliver beneficial compounds, including chelators, may have additional components that are particularly helpful to that end. In particular, these compositions contain nanoparticulate silica scaffolds that provide hydrogen bonding for many of such beneficial compounds and can be induced to release such compounds under the conditions of the digestive tract. It is desirable to have these compounds released in the duodenum or small intestine as opposed to the stomach which has a very low pH and little absorptive capacity into the circulatory system. As described in Dressman, J. B., et al., *Pharm. Res.* (1990) 7:756-761, in a typical study, the pH of the stomach in the fasted state is 1.7 and the median duodenal pH is 6.1. After administering a meal, the gastric pH climbed briefly to a peak value of 6.7 and then declined gradually back to the fasted state over a period less than 2 hours. The duodenal pH after a meal was reduced to 5.4 and returned more slowly to the fasted state. Similar results were obtained by Rune, S. J., et al., *Gut* (1969) 10:569-571. It may be desirable to include an enteric coating so that the bolus of the composition can survive the transit through the stomach into the duodenum where it can be absorbed. These are discussed below.

Nanoparticulate Silica-Based Components

A very effective carrier for compounds to be delivered from the digestive system comprises fumed silica.

Fumed silica is particularly helpful as it has other desirable properties. These include hydrogen bonding of surface-rich hydroxyl groups to each other and through polar water. Short chains of 10-20 nm sized nanoparticles are formed in untreated fumed silica as well as aggregation of short chains to produce a three-dimensional labyrinth to result in reassortment upon shear. The powder is highly hydrophilic, has low moisture content and is amorphous. It absorbs water upon hydration, but is insoluble, chemically inert, non-toxic, and generally recognized as safe (GRAS). Addition of up to 20% alumina results in thickening of aqueous solutions (seen at a maximum at 16%).

Some embodiments include untreated Cab-O-Sil™ fumed silica products from Cabot Corporation, or fumed silica from Degussa, which are fine white powders with a specific gravity of 2.2. They are typically 99.8% pure silica by weight and are very suitable for use in adhesives. The surface chemistry of Cab-O-Sil™ fumed silica influences moisture content, reinforcement properties and rheology control. The chemical groups on the surface of untreated Cab-O-Sil™ fumed silicas are isolated silanol and hydrogen-bonded silanol that are both hydrophilic, and the inserted siloxane group that is hydrophobic. Cab-O-Sil™ fumed silica imparts viscosity build-up and flow control properties to polymer systems by forming a three dimensional interacting network of silica aggregates throughout the system. The aggregates interact with one another through the hydrogen bonding of their surface silanol groups restricting the flow and increasing the viscosity of the system. If the fumed silica is stirred, many of the hydrogen bonds are broken, the system loses viscosity and it becomes easier to coat surfaces or extrude from a tube. As soon as the shearing force is removed, the hydrogen bonds begin to reform and the viscosity of the system increases again.

Additives can be used with Cab O Sil™ fumed silica to enhance the network through the formation of additional bridges to increase viscosity.

Cabot Corporation supplies a number of different fumed silica products suitable for use and includes various products with a large hydrophilic surface area: Cab O Sil™ EH-5 (380 $m^2/g$ of surface area), Cab O Sil™ HS-5 (325 $m^2/g$ of surface area), Cab O Sil™ M-5P (200 $m^2/g$ of surface area), Cab O Sil™ M-5 (200 $m^2/g$ of surface area), Cab O Sil™ PTG (200 $m^2/g$ of surface area), Cab O Sil™ MS-55 (255 $m^2/g$ of surface area), Cab O Sil™ LM-150 (160 $m^2/g$ of surface area).

Degussa provides a series of AEROSIL fumed silica products that include: AEROSIL COX 84, VP AEROPERL 300 Pharma (300 $m^2/g$ of surface area), AEROSIL 200 (200 $m^2/g$ of surface area), AEROSIL 200 VV Pharma (200 $m^2/g$ of surface area), AEROSIL MOX 170, and AEROSIL MOX 80.

The compositions of the invention may include these silica nanoparticles that when mixed will cross-bridge and polymerize to form a hydrogen-bonded lattice or scaffolding, and could be considered. In some embodiments, the particles have surface area as high as 500 $m^2/g$ and an average of eight (8) hydroxyl groups per $nm^2$ (range 1-20). These nanoparticles are extremely small (from about 0.01 nanometers to about 1 micrometer in diameter). The small size coupled with the large surface area allows for an excessive number of reactive hydroxyl groups to facilitate cross linking in the highly polar water environment.

These nanoparticles should not be confused with larger chemically-inert silica macro- or microparticles (greater than 1 micrometer in diameter), which are produced by grinding and sieving, and are commonly used in the food industry for anti-caking purposes. The conventional larger silica particles lack the necessary active hydroxyl functional groups on the surface of the particle.

In some embodiments, these carriers have surface areas up to about 500 $m^2/g$, and with individual particle sizes as small as a few nanometers in diameter. Medical grade fumed silica for human use is relatively rare (e.g., Cabot sells Cab O Sil™ grades M5 or MSP suitable for human applications). For other applications where medical grade quality is not as critical (e.g., life threatening trauma or battlefield conditions), Cabot grades L-90, LM-130, LM-150, PTG, M-7D, MS-55, H-5, HS-5, or EH-5 may be used. All grades fall within the range of 90-380 $m^2/g$ average surface areas, less than 0.02% 325 mesh residue (44 microns), a size less than 100 nanometers, and have appropriate reactive surface chemistry.

Fumed silica is produced by hydrolysis of silicon tetrachloride in a hydrogen oxygen flame at 1800° C. that results in a surface density of hydroxyl groups average 4 hydroxyls per square nanometer.

The silica-based carriers have the following properties:

When hydrated, they instantly agglomerate into supramolecular networks, or fabric, of cross-bridging chains of silicon dioxide, in a lattice form that provides a three dimensional framework for incorporating moieties with dimensions below one micron. This dimension of the three dimensional framework permits incorporating a high capacity of moieties, such as the ceramic heavy metal cation exchangers.

If the composition is ingested, the water used in formulation and present in the stomach participates in the creation of the lattice thus serving for both a) the three dimensional lattice formation for embedding and sequestering passenger agents and b) the water absorption (by hydrogen bonding as part of the lattice structure itself) resulting in thickening.

The three-dimensional lattice will cause the fluid to become a thixotropic gel in the absence of shear forces, therefore serving as a flexible pliable hydrogel that continually reforms itself in response to shear forces from gastrointestinal motility.

The non-porous fumed silica is also a convenient non-interactive carrier of other optional components to enhance oral delivery. (The bridging/binding agent is itself a useful oral drug delivery agent.)

Silica can be used as long or short chains of agglomerated nanoparticles ranging in surface area from 25 $m^2/g$ to 500 $m^2/g$ or greater or about 200 $m^2/g$. The degree of network formation is dependent upon several factors that can be controlled either through the formulation and compounding or in the method of application at time of use. The grades and concentrations described herein are workable.

For orally administered compositions, the pH in the stomach and the gastrointestinal tract are important. A pH of greater than 2.3 up to 8 is suitable. The isoelectric point for nanosilica is approximately 2.3. The degree of dispersion in the stomach and in the small intestine is also important. The high hydrophilicity of reactive silica nanoparticles for water in the stomach routinely assures the 'draw-in' of aqueous fluid into the admixture once ingested as a powder, a gel, or as a non-aqueous liquid. This assures adequate and rapid dispersion. The use of nonaqueous based liquid formulations is also effective as aqueous fluid from the stomach is drawn into the admixture to assure adequate dispersion even for these.

Components that Assist in Effecting Bolus Gel Formation for Oral Administration

Compositions of the invention that are designed for oral administration typically contain thickening agents and/or gel-forming/fluid removal agents. Typical embodiments of these are described below.

Thickening Agents

Thickening agents are effective rheology modifiers that produce very high viscosities (up to 2200 cps at 5% solids). The thickening agent may be very highly hydrophilic and expand upon absorption of water (>20:1 up to 600:1). These agents are provided as microfine powders or are granular in form with mesh size >100 (149 microns), have low moisture contents, and are amorphous and insoluble. The thickening agents used in the invention compositions absorb water upon hydration, are chemically inert, are naturally occurring, are non-toxic, and are generally regarded as safe (GRAS).

For example, Grain Processing Corp (GPC) provides Waterlock™ superabsorbent starch copolymers as thickening agents. Starch graft 20 mesh polymers Waterlock™ G-430 (swell rate 500 plus) and Waterlock™ G-400 (swell rate 600) are superabsorbent polymers composed of poly(2-propenamide-co-2-propenoic acid, sodium salt). Additional GPC Waterlock™ products provide superabsorbent starch graft copolymers of poly(2-propenamide-co-2-propenoic acid), which are available as sodium or potassium salts and include Waterlock™ A100 (20 mesh, swell rate 130-200 plus), Waterlock™ A180 (20 mesh, swell rate 120-200 plus), and Waterlock™ A220 (40-60 mesh, swell rate 300-350 plus). Another useful material is Reon®, produced by Absorbent Technologies, Inc.; again compounded of superabsorbent starch polymers.

The American Colloid Company (ACC), Arlington Heights, Ill. provides industrial specialty clays as thickening agents including Bentobrite® 770 which is a natural white sodium bentonite, Montmorillonite natural clay provided as a micronized powder (325 mesh, dry processed sodium and calcium bentonite). Also, ACC provides VOLCLAY® 325 mesh and VOLCLAY® HPM75 dry processed microfine sodium bentonite.

AMCOL® Health and Beauty Solutions, Inc. (AMCOL®) provides thickening agents that are highly purified pharmaceutical grade Magnesium Aluminum Silicates, MAGNABRITE HV (high viscosity), selected blend of white smectite clays (Mg Al silicate mineral) that provide viscosities of 800-2200 cps at 5%. AMCOL® also provides highly purified white bentonites and functional hydrogels such as POLARGEL® VOLCLAY® NF-BC pharmaceutical grade, irradiated, and water washed. This product includes sodium and calcium bentonite, montmorillonite clay powder with a swelling power of 24 ml/gm. Additionally, AMCOL® provides highly purified white bentonites and functional hydrogels as POLARGEL® IVP which is water washed, surface modified sodium Montmorillonite clay plus intercalated organic polymer, INCI PVP, which is designed to build viscosity in polar aqueous solvents (325 mesh, powder). Super absorbent polymers, as used in diapers, are also available as sodium salts of polyacrylic acid, co-polymerized with acrylamide and ethylenebis (acrylamide).

AMCOL® also provides a highly adsorptive polymer, POLY-PORE® E200, which is an allyl methacrylate cross polymer as a white free flowing powder (20 micron). This multi-functional adsorbent polymer helps to stabilize and protect sensitive ingredients from degradation. It is simultaneously both hydrophilic and lipophilic actives create an almost endless range of delivery systems where it can be used to stabilize and protect actives or control the rate of delivery while targeting the site of action.

Qingdao Makall Group Co. Ltd. (Makall), Qingdao, China provides silica gel products that are composed of very highly adsorptive material as a thickening agent. These products are amorphous substances that are insoluble in water and other solvents, are nontoxic, and are chemically stable. The various types of silica gels formulated by Makall have different pore structures with unique chemical compositions and physical structures. These products are distinguished with high adsorption features, stable thermal performance, stable physical properties, and relatively high mechanical strengths. Makall Silica Gel products are differentiated according to their pore diameters. Makall Narrow Pore Silica Gels (SG01/SG02) are described as comprised of bead sizes from 1.4 to 8.0 mm which contain an inner structure of pore volume 0.35-0.45 ml/g, pore diameter of 2 to 3 nm and surface area of >600 m²/g. Makall Middle Pore Silica Gels (SG03/SG04) are described as comprised of bead sizes from 2.0 to 8.0 mm which contain an inner structure of pore volume 0.5-0.8 ml/g, pore diameter of 5 to 8 nm and surface area of 450-600 m²/g. Makall Wide Pore Silica Gels (SG05/SG06) are composed of bead sizes from 1.4-8.0 mm which contain an inner structure of pore volume 0.78-0.1.00 ml/g, pore diameter of 8-10 nm and surface area of 350-500 m²/g. Also note all ACC/AM-COL®/CETCO products are available irradiated.

Gelling Agents

Other optional components of the carrier include gelling agents. These absorb fluids rapidly and retain them in an inner core without separation even though remaining in fluid media. The material should be a desiccant, a highly hydrophilic powder with porous microspheres of an average diameter of 20-35 microns. Other characteristics include low moisture content, amorphous structure, and ability to absorb water upon hydration. The gelling agent should be chemically inert, non-toxic, and generally recognized as safe (GRAS).

Dry, flocculent, neutral, anionic or cationic, cross-linked polyamine, polyDADMAC, or polyacrylamide (Cytec, Inc., SUPERFLOC®) is one example and can aid as a mordant. These are available in a variety of molecular weights of varying viscosity. Lignosulfates are naturally occurring GRAS materials extracted from wood pulp by various processes and are used in animal feeds and as indirect food additives. They occur in polymeric form following digestion and are hydrophilic and are used as adhesives, binders and sequestrants. Hyaluron is a GRAS linear polysaccharide used in cosmetics, and is one component suitable for the invention compositions.

Enteric Coatings

An enteric-coated "carrier" is designed to carry dry particles through the low pH environment of the stomach and release the particles within the higher pH environment found in the lumen of the large and small intestine. The composition then binds to the mucosal lining of the GI tract.

An enteric coating is applied by film coating technology to either tablets or capsules to protect the product in the gastric environment. Such coatings are those that remain intact in the stomach, but will dissolve and release the contents of the dosage form once it reaches the small intestine.

Enteric polymers include cellulose acetate phthalate (CAP) and polyvinyl acetate phthalate (PVAP), which is less permeable to moisture, more stable to hydrolysis, and able to ionize at a lower pH than is CAP. Other enteric polymers include methacrylic acid-methacrylic acid ester copolymers with acid ionizable groups, such as those trade-named Eudragit available through Rohm Pharma. Generally, the enteric coating will be applied from about 0.5% by weight to about 10% by weight of the tablet or capsule.

In addition to the outer protective enteric coating, the chambers in which drug and other excipients are located on the particles can contain a protective cover or layer of material. This material can be a water-soluble substance such as cellulosic derivative like hydroxypropyl methylcellulose or gelatin, or a less water-soluble polymer such as methylcellulose.

"ChronSet®" technology developed by ALZA Corporation (Mt. View, Calif.) can be used to release a bolus of the compositions at designated times and at targeted absorption sites after passage from the stomach into the small intestine. In this case, a suspension of particles is loaded into ChronSet® capsules. After swallowing, the capsules pass intact through the stomach. The shell is engineered to regulate the rate of water imbibition through the osmotically permeable portion of the system. The osmotic engine expands to push and separate two halves of the capsule. The length of the capsule halves is specifically designed to produce separation at pre-selected times. The contents of each capsule are expelled into the intestinal lumen at 2 to 20 hours after administration. Greater than 80% of contents (in this case a suspension of drug-filled microfabricated particles) are expelled within 15 minutes timeframe.

Summary

In summary, some of the invention compositions are designed for heavy metal remediation generally and these contain a nanoparticulate ceramic cation exchanger in the presence of a carrier which may include additional sorbents, gelling agents, thickening agents, and beneficial compounds including chelators and the like. Depending on the application for which the composition is designed, the carrier will be modified to be appropriate to the application. If designed for application in the environment generally, and if the composition, having removed the heavy metal from a specific target, can be recovered so that a decontaminated foodstuff, for example, can be ingested without the presence of the invention composition, the composition need not be nontoxic nor need it be suitable for oral administration. However, if used in the environment to decontaminate a foodstuff where the composition remains associated with the foodstuff, or if the composition is designed for remediation in a human or other animal subject, the composition must be suitable for oral administration.

An advantageous form of oral administration includes agents in the carrier that effect gelling, thickening, and generally absorb water so that the composition will pass readily through the digestive tract and be excreted. If beneficial compounds are to be delivered, the compositions should also include cross-binding agents such as nanoparticulate fumed silica nanocages. The fumed silica may also aid in the thickening and gelling of the composition.

Because the compositions of the invention are multicomponent mixtures, additional factors may be necessary to aid in formulation. These additional materials may control pH, ionic strength, and the like.

Generally, the compositions of the invention, if designed for oral administration, will be decontaminated, sterilized or otherwise rendered free of infectious organisms.

As noted above, in some embodiments, the oral delivery systems of the invention provide optimized delivery of compounds for gastrointestinal uptake. They deliver constituents to the area of the gastrointestinal tract at which it is best absorbed, and overcome physiological, biochemical, and other factors that are obstacles to optimally transfer the constituents. Suitable formulations unpackage the constituents at the desired site of use, in a manner that optimally supports absorption by the body through the lining of the gastrointestinal tract.

Applications

The compositions of the invention have a variety of applications and the design of a specific composition is, of course, adapted to the application for which it is intended.

In one important application, foods or water or other liquids are decontaminated using the invention compositions prior to ingestion. While chelators may be included in these claims, strictly speaking, they are not necessary. If the composition is not removed from the water or food prior to ingestion, the composition must be nontoxic and suitable for oral administration. For example, if it is applied to a solid food and can be washed away prior to the ingestion of the food, lack of toxicity is no longer needed.

In some applications of the invention, the heavy metal ions are simply absorbed into the composition and pass through the digestive tract and are excreted.

In some embodiments, the compositions are also designed for ingestion to remediate heavy metal poisoning where the heavy metals have remained in the digestive tract. These compositions are designed to simply absorb the metal, pass through the digestive tract, and be excreted.

However, if the heavy metals have penetrated to the body outside the digestive system, a more complex composition is needed which will provide chelating agents that can be absorbed from the digestive tract. In this case, the compositions are designed to swell in the stomach or small intestine and preferably to adhere to the walls of the tract and to facilitate delivery of the chelating agent which then can circulate, chelate the offending heavy metals, and effect excretion through the kidney.

For any composition designed for oral administration, it is also possible to add beneficial agents that can be absorbed from the digestive system into parenteral areas. Indeed, some compositions of the invention are designed specifically to deliver beneficial compounds rather than remediate heavy metal contamination.

The subjects to which oral administration is appropriate include animal subjects in general not only humans but other primates, livestock, companion animals, such as cats and dogs. Livestock include pigs, goats, bovines, horses and the like. Aquatic species such as fish, crustaceous, bivalves and the like can be used. In addition, laboratory animals such as rats and mice may be the subjects as they are useful in studying the effects of the invention compositions.

Oral administration may be by direct administration to the above species through medicaments, oral fluid, feed, and the like, or by indirect oral administration through pretreatment of oral fluids or feed, or pretreatment of soil for food crops or silage, and the like.

The invention in its various embodiments is described as follows:

The invention is directed to a composition that sorbs heavy metals which comprises a ceramic nanoparticulate cation exchanger for at least one heavy metal and at least one carrier.

In some embodiments, the composition is suitable for oral consumption, and wherein the carrier forms a gel mass in aqueous medium, and/or which is non-toxic.

In the above compositions, the carrier may comprise an additional sorbent for heavy metals, and in some embodiments, the additional sorbent is activated charcoal, derivatized chitosan, a heavy metal-absorbing plant material, a fumed silica, a zeolite, bentonite or combinations thereof.

In some embodiments suitable for oral consumption, the carrier comprises an agent for improving the handling properties of the composition and/or the behavior of the composition in the digestive tract, wherein said agent may be a cross-binding agent, fluid-removal agent/gel-forming agent and a thickening agent or mixtures thereof.

The compositions described above may contain a heavy metal chelator. The compositions are useful in methods to decontaminate a comestible which method comprises treating the comestible with any of said compositions.

The compositions that are nontoxic are suitable in methods for prophylactically treating a subject to prevent absorption of heavy metals from the digestive tract, by administering, orally, to said subject these compositions.

Especially useful in methods to treat subjects who have ingested heavy metal are compositions containing a chelator. The invention methods include administering them orally to said subject.

Various specific compositions are as follows: A composition which comprises 50% (w/w) ATS Adsorbent mercury selective cationic ion exchanger (Engelhard), 50% (w/w) N-[3-(methylthio)propyl]-chitosan (MTPC) and further contains food flavorings to produce a marinade, a composition which is a gelatin capsule containing (25% w/w) ATS adsorbent, mercury selective cationic ion exchange (Engelhard), (25% w/w) activated Charcoal, 25% (w/w) Pharmasorb® attapulgite, colloidal (Engelhard), and (25% w/w) *Azolla filiculoides*, root extract, granular, dry powder bio-adsorbent, a composition which is a gelatin capsule containing 50% (w/w) ATS Adsorbent, mercury selective cationic ion exchanger (Engelhard), 40% (w/w) N-[3-(methylthio)propyl]-chitosan (MTPC), and (10% w/w) M5 fumed silica (Cabot) pharmaceutical grade, a composition which is a gelatin capsule containing 80% (w/w) ATS ceramic adsorbent, lead selective cationic ion exchanger (Engelhard), and 20% (w/w) activated charcoal, pharmaceutical grade, a composition which is a gelatin capsule containing 80% (w/w) ARM 200, arsenic selective, ion exchange adsorbent (Engelhard), and 20% (w/w) activated charcoal, pharmaceutical grade, and a composition which is a gelatin capsule containing 80% (w/w) ARM 200 ceramic, arsenic selective, cationic ion exchange powder (Engelhard), and 20% (w/w) carboxymethylcellulose, pharmaceutical grade, or equivalent.

In another embodiment, the compositions are for oral delivery of beneficial compounds by absorption into the body from the digestive system, wherein the compositions comprise a nanoparticulate silica-based scaffold having a surface area of at least 50 $m^2/g$, at least one beneficial compound, a miscibility agent, and a carrier that forms a gel mass in aqueous media.

The invention includes the above composition wherein the nanoparticulate silica scaffold has a surface area of at least 380 $m^2/g$, and/or wherein said scaffold has been treated with a mucoadhesive agent, and/or wherein the miscibility agent is polyethylene glycol or polysorbate ester, and/or wherein said carrier contains a thickening agent and/or a fluid removal/gel-forming agent.

The thickening agents may comprise starch copolymers or clays, and the fluid removal/gel-forming agent may be a crosslinked polyamine or polyacrylamide.

The beneficial compound is a vitamin, pharmaceutical, or chelating agent, and any of the compositions can be enclosed in an enteric coating.

These compositions are useful in a method to deliver beneficial compounds to a subject through the digestive tract which method comprises administering an effective amount of them to the digestive tract of the subject.

In this case, the composition may be administered as a tablet, capsule or chewing gum.

In the compositions that sorb heavy metals which comprise a ceramic nanoparticulate cation exchanger for at least one heavy metal and at least one carrier, and which is suitable for oral consumption. The carrier is delivered in aqueous medium.

The carrier may comprise an additional sorbent for heavy metals. The additional sorbent may be activated charcoal, derivatized chitosan, a heavy metal-absorbing plant material, a fumed silica, a zeolite, bentonite or combinations thereof. The compositions may further contain a heavy metal chelator.

These compositions of the invention are useful in a method to decontaminate a pond, reservoir, lake, stream, estuary or other body of water which method comprises treating said body of water with said composition, especially wherein the composition is nontoxic or suitable for oral consumption by species living in or about the body of water and/or otherwise consuming the water from that body of water, and/or the composition is nontoxic to, or suitable for oral consumption by species on or about an area of land used for raising of crops for food or silage.

Specific embodiments include a composition which is 5% (w/w) ATS Adsorbent mercury selective cationic ion exchanger (Engelhard), 10% (w/w) ARM 200, arsenic selective, ion exchange adsorbent (Engelhard), (25% w/w) *Azolla filiculoides*, root, and 60% (w/w) of ZK406H, a natural clinoptilolite form of potassium aluminosilicate, (St. Cloud Mining Company), and a composition which is 50% (w/w) ATS Adsorbent, selective cationic ion exchanger (Engelhard), and 50% (w/w) ZK406H, a natural clinoptilolite form of potassium aluminosilicate, (St. Cloud Mining Company).

The following examples are offered to illustrate but not to limit the invention.

EXAMPLE 1

Mercury Heavy Metal Removal from Raw Seafood

An admixture of the following materials is mixed with suitable herbs and seasonings blend and is used as a dry or aqueous marinade. The basic heavy metal admixture for Hg removal from fish (to be mixed with flavorings) would be composed of the following powders:

50% wt/wt ATS Adsorbent, mercury selective cationic ion exchanger (Engelhard) and 50% wt/wt N-[3-(methylthio)propyl]-chitosan (MTPC).

EXAMPLE 2

Mercury Heavy Metal Removal from Humans (Prior to Ingestion and/or Intestinal Absorption)

The following gelatin capsule would be taken up to two hours before ingestion of seafood for removal of mercury through ion exchange prior to minimize intestinal adsorption. The capsule would be taken orally with water. The capsule may also be taken right after ingestion, or up to 2 hours, post-ingestion.

Capsule Contents: (25% w/w) ATS adsorbent, mercury selective cationic ion exchange (Engelhard), (25% w/w) activated Charcoal, 25% (w/w) Pharmasorb® attapulgite, colloidal (Engelhard), and (25% w/w) *Azolla filiculoides*, root extract, granular, dry powder bio-adsorbent.

EXAMPLE 3

Heavy Metal Treatment for Mercury

This composition is for use either to prophylactically prevent or reduce adsorption, and/or post adsorption to reduce circulating plasma levels of mercury in humans. It is taken as a gelatin capsule on a regular regime orally to either prophylactically prevent or reduce adsorption, and/or post adsorption to reduce circulating plasma levels of mercury in humans. The dry admixture contains both heavy metal removing agents in addition to bulk fiber. Bulk fiber is supplied through the use of a variety of rapidly rehydratable bulking agents safe for human ingestion, including but not limited to: carboxymethylcellulose; cellulose; chitosan; (expand here); and the like. An alternative to bulk fiber is the use of highly hydrophilic hydrated silica nano-particles that produce a viscous gelatinous mass upon primary hydration. The gelatinous mass is produced after the pH shift down observed in the stomach, followed by the subsequent pH shift up observed in the duodenum.

50% (w/w) ATS Adsorbent, mercury selective cationic ion exchanger (Engelhard), 40% (w/w) N-[3-(methylthio)propyl]-chitosan (MTPC), and (10% w/w) M5 fumed silica (Cabot) pharmaceutical grade).

EXAMPLE 4

For Lead and or Mercury Heavy Acute Poisoning (Pre Internal Absorption)

This formulation is used for acute lead or mercury poisoning and employs a lead or mercury specific cationic ion exchange-coupled-with activated charcoal for rapid active adsorption of lead and mercury by ion exchange. Upon contact a gelatin capsule comprising of the following admixture would be taken orally after exposure with water and repeated every 2-4 hours for 24 hours.

Each Capsule contains: 80% (w/w) ATS ceramic adsorbent, lead selective cationic ion exchanger (Engelhard), and 20% (w/w) activated charcoal, pharmaceutical grade.

EXAMPLE 5

Lead Heavy Metal Removal Post Absorption Internally

This is utilized to reduce circulating blood levels of lead post adsorption. It could also be used prophylactically on an intermittent basis to minimize adsorption due to exposure over time especially in children.

Each Capsule contains: 80% (w/w) ATS ceramic adsorbent lead-selective cationic ion exchanger (Engelhard), and 20% (w/w) carboxymethylcellulose, or equivalent

EXAMPLE 6

Arsenic Heavy Metal Removal Post Exposure but Pre-Adsorption

This is utilized to actively reduce and/or prevent intestinal adsorption of arsenic following an acute exposure episode.

Each capsule contains: 80% (w/w) ARM 200, arsenic selective, ion exchange adsorbent (Engelhard), and 20% (w/w) activated charcoal, pharmaceutical grade.

EXAMPLE 7

Arsenic Heavy Metal Removal

This is a prophylactic use to prevent absorption, or post absorption to reduce circulating levels). It is used over time to reduce absorption of low levels of arsenic found in drinking water or post absorption to reduce circulating blood levels through intestinal absorption.

Each capsule would contain: 80% (w/w) ARM 200 ceramic, arsenic selective, cationic ion exchange powder (Engelhard), and 20% (w/w) carboxymethylcellulose, pharmaceutical grade, or equivalent

EXAMPLE 8

Lead Heavy Metal Removal

A stock solution containing the 40 mg/L of lead was prepared and serial by diluted into 4 equal aliquots of 5 liters each. Then 20 ug/L of ATS ceramic adsorbent lead-selective cationic ion exchanger (Engelhard) was broadcast onto the surface of the solution and permitted to settle by gravity. Samples of the solution were taken at the indicated intervals and submitted for Mass Spec analysis. Experiments were conducted both without (data shown) and with carriers (data not shown). Statistical differences were not observed between carrier and non-carrier compositions.

| Lead (mg/L) | ATS (ug/L) | Time of Sample Collection (min) | | | | |
|---|---|---|---|---|---|---|
| | | 0 | 30 | 90 | 180 | 360 |
| | | Concentration (ug/L) | | | | |
| 5 | 20 | 13.7 | 5.96 | 3.31 | 3.31 | 1.25 |
| 10 | 20 | 13.7 | 4.34 | 2.54 | 2.14 | 3 |
| 20 | 20 | 13.7 | 3.81 | 3.58 | 3.07 | 3.37 |
| 40 | 20 | 13.7 | 2.98 | 1.3 | 1.41 | .99 |

The ATS formulation effectively removed the lead in the aqueous sample and brings the concentration down to below the EPA guideline of 15 ppb.

EXAMPLE 9

Mercury Heavy Metal Removal

A stock solution containing the 80 mg/L of lead was prepared and serially diluted into 4 equal aliquots of 5 liters each. Then 20 ug/L of ATS ceramic adsorbent lead-selective cationic ion exchanger (Engelhard) was broadcast onto the surface of the solution and permitted to settle by gravity. Samples of the solution were taken at the indicated intervals and submitted for Mass Spec analysis.

| Hg (mg/L) | ATS (ug/L) | Time of Sample Collection (min) | | | | |
|---|---|---|---|---|---|---|
| | | 0 | 30 | 90 | 180 | 360 |
| | | Concentration (ug/L) | | | | |
| 10 | 20 | 18.5 | 17.2 | 16.8 | 13.2 | 10.1 |
| 20 | 20 | 18.5 | 9.24 | 7.95 | 7.52 | 5.96 |
| 40 | 20 | 18.5 | 5.58 | 4.18 | 3.58 | 2.96 |
| 80 | 20 | 18.5 | 3.72 | 2.92 | 2.1 | 1.97 |

The ATS formulation effectively removed the mercury in the aqueous sample and brings the concentration down to below the EPA guideline of 2 ppb at the longer times.

EXAMPLE 10

Arsenic Heavy Metal Removal

A stock solution containing the 160 mg/L of arsenic was prepared and serially diluted into 4 equal aliquots of 5 liters each. Then 20 ug/L of ARM 200, arsenic selective, ion exchange adsorbent (Engelhard) were then broadcast onto the surface of the solution and permitted to settle by gravity. Samples of the solution were taken at the indicated intervals and submitted for Mass Spec analysis.

| Hg (mg/L) | ATS (ug/L) | Time of Sample Collection (min) | | | | |
|---|---|---|---|---|---|---|
| | | 0 | 30 | 90 | 180 | 360 |
| | | Concentration (ug/L) | | | | |
| 20 | 20 | 21.2 | 20.2 | 19.4 | 19 | 17.7 |
| 40 | 20 | 21.2 | 18.7 | 18.7 | 18.3 | 18.3 |
| 80 | 20 | 21.2 | 17.2 | 17 | 16.8 | 16.4 |
| 160 | 20 | 21.2 | 14.2 | 14.8 | 14.3 | 14 |

The ARM formulation removed the arsenic in the aqueous sample and but did not bring the concentration down to below the EPA guideline of 10 ppb. This is most likely due to the larger particle size (<80 mesh) of this formulation. Much higher adsorption would be expected with smaller particles or with mixing the solution.

EXAMPLE 11

Removal of Heavy Metal Mixtures from Contaminated Ponds, Reservoirs, Lakes, Streams, Estuaries and Other Bodies of Water The following composition is broadcast of the surface of any body of water, moving or stagnant, in order to eliminate heavy metals. The composition is adjusted to focus specifically on one heavy metal or on a mixture of heavy metals. The primary focus of this admixture is arsenic, lead, mercury but other heavy metals such as cadmium, chromium, etc., as well as zinc and copper will also be adsorbed. Upon contact with the water, the material settles through the water column and captures the metals in a passive manner for still water, but also captures the same metals but in a more efficient manner for flowing water. The admixture is composed of the following materials:

5% (w/w) ATS Adsorbent mercury selective cationic ion exchanger (Engelhard), 10% (w/w) ARM 200, arsenic selective, ion exchange adsorbent (Engelhard), (25% w/w) *Azolla filiculoides*, root, and 60% (w/w) of ZK406H, a natural clinoptilolite form of potassium aluminosilicate, (St. Cloud Mining Company).

EXAMPLE 12

Removal of Mercury and Lead from Aquaculture Use (Fish, Shellfish, Etc.)

This composition is for use either to prevent prophylactically or reduce adsorption by any aquatic species, and/or to reduce circulating levels of mercury or lead in the growing water medium. The dry admixture contains both heavy metal removing agents in addition to filler. The filler is supplied through the use of a rapidly rehydratable bulking agents safe for ingestion. The admixture may be added to the feed of the aquatic species or broadcast throughout the aqueous medium.

The composition is composed of: 50% (w/w) ATS Adsorbent selective cationic ion exchanger (Engelhard), and 50% (w/w) ZK406H, a natural clinoptilolite form of potassium aluminosilicate, (St. Cloud Mining Company).

EXAMPLE 13

Animal Feed Use for Heavy Metal Free Animals

This composition is for use either to prevent prophylactically or to reduce adsorption by the animal, and/or to reduce animal circulating levels of heavy metal from contaminated feed and/or water ingested. The dry admixture contains both heavy metal removing agents in addition to filler. The admixture may be added to the feed to promote stronger bone development, greater weight gain and increased feed efficiency values.

This composition is composed of: 30% (w/w) ATS Adsorbent selective cationic ion exchanger (Engelhard), and 65% (w/w) ZK406H, a natural clinoptilolite form of potassium aluminosilicate, (St. Cloud Mining Company), and 5% (w/w) fumed silica (DeGussa), a thixotropic bulking agent.

EXAMPLE 14

Field Application to Animal Feed or Food Crops Permitting Harvesting from Contaminated Soil This composition is for use to prevent or reduce adsorption by humans or animals, by either treating the contaminated soil or actual crop prior to harvest. The dry admixture contains both heavy metal removing agents in addition to filler. The filler is supplied through the use of a rapidly rehydratable bulking agents The composition is composed of: 10% (w/w) ATS Adsorbent selective cationic ion exchanger (Engelhard), 60% (w/w) ZK406H a natural clinoptilolite form of potassium aluminosilicate, (St. Cloud Mining Company) and (30% w/w) *Azolla filiculoides*, root.

The invention claimed is:

1. A composition that sorbs heavy metals which comprises a ceramic nanoparticulate cation exchanger for at least one heavy metal and at least one carrier Wherein said carrier forms a gel mass in aqueous medium, and is non-toxic.

2. The composition of claim 1 wherein said carrier comprises an additional sorbent for heavy metals.

3. The composition of claim 2 wherein said additional sorbent is activated charcoal, derivatized chitosan, a heavy metal-absorbing plant material, a fumed silica, a zeolite, bentonite or combinations thereof.

4. The composition of claim 1 wherein said carrier comprises an agent for improving the handling properties of the composition and/or the behavior of the composition in the digestive tract.

5. The composition of claim 4 wherein said agent is a cross-binding agent, fluid-removal agent/gel-forming agent and a thickening agent or mixtures thereof.

6. The composition of claim 1 which further contains a heavy metal chelator.

7. The composition of claim 1 which comprises 50% (w/w) ATS Adsorbent mercury selective cationic ion exchanger (Engelhard), 50% (w/w) N-[3-(methylthio)propyl]-chitosan (MTPC) and further contains food flavorings to produce a marinade, or which is a gelatin capsule containing (25% w/w) ATS adsorbent, mercury selective cationic ion exchange (Engelhard), (25% w/w) activated Charcoal, 25% (w/w) Pharmasorb® attapulgite, colloidal (Engelhard), and (25% w/w) *Azolla filiculoides*, root extract, granular, dry powder bio-adsorbent, or which is a gelatin capsule containing 50% (w/w) ATS Adsorbent, mercury selective cationic ion exchanger (Engelhard), 40% (w/w) N-[3-(methylthio)propyl]-chitosan (MTPC), and (10% w/w) M5 fumed silica (Cabot) pharmaceutical grade, or which is a gelatin capsule containing 80% (w/w) ATS ceramic adsorbent, lead selective cationic ion exchanger (Engelhard), and 20% (w/w) activated charcoal, pharmaceutical grade, or which is a gelatin capsule containing 80% (w/w) ARM 200, arsenic selective, ion exchange adsorbent (Engelhard), and 20% (w/w) activated charcoal, pharmaceutical grade, or which is a gelatin capsule containing 80% (w/w) ARM 200 ceramic, arsenic selective, cationic ion exchange powder (Engelhard), and 20% (w/w) carboxymethylcellulose, pharmaceutical grade, or equivalent.

8. A composition for oral delivery of beneficial compounds by absorption into the body from the digestive system, which composition comprises a nanoparticulate silica-based scaffold having a surface area of at least 50 $m^2/g$, at least one beneficial compound, a miscibility agent, and a carrier that forms a gel mass in aqueous media.

9. The composition of claim 8, wherein the nanoparticulate silica scaffold has a surface area of at least 380 $m^2/g$, and/or wherein said scaffold has been treated with a mucoadhesive agent, and/or wherein the miscibility agent is polyethylene glycol or polysorbate ester, and/or wherein said carrier contains a thickening agent and/or a fluid removal/gel-forming agent.

10. The composition of claim 9, wherein the thickening agent comprises starch copolymers or clays, and/or wherein the fluid removal/gel-forming agent is a crosslinked polyamine or polyacrylamide.

11. The composition of claim 8, wherein said beneficial compound is a vitamin, pharmaceutical, or chelating agent.

12. The composition of claim 8, which further is enclosed in an enteric coating.

13. The composition of claim 1, which is suitable for oral consumption, and wherein said carrier is delivered in aqueous medium.

14. The composition of claim 13, wherein said carrier comprises an additional sorbent for heavy metals.

15. The composition of claim 14, wherein said additional sorbent is activated charcoal, derivatized chitosan, a heavy metal-absorbing plant material, a fumed silica, a zeolite, bentonite or combinations thereof.

16. The composition of claim 13, which further contains a heavy metal chelator.

17. The composition of claim 13, which is 5% (w/w) ATS Adsorbent mercury selective cationic ion exchanger (Engelhard), 10% (w/w) ARM 200, arsenic selective, ion exchange adsorbent (Engelhard), (25% w/w) *Azolla filiculoides*, root, and 60% (w/w) of ZK406H, a natural clinoptilolite form of potassium aluminosilicate, (St. Cloud Mining Company), or which is 50% (w/w) ATS Adsorbent, selective cationic ion exchanger (Engelhard), and 50% (w/w) ZK406H, a natural clinoptilolite form of potassium aluminosilicate, (St. Cloud Mining Company).

* * * * *